United States Patent [19]

Barrera et al.

[11] Patent Number: 5,399,665
[45] Date of Patent: Mar. 21, 1995

[54] BIODEGRADABLE POLYMERS FOR CELL TRANSPLANTATION

[75] Inventors: Denise Barrera, Oakdale, Minn.; Robert S. Langer, Newton, Mass.; Peter T. Lansbury, Jr., Brookline, Mass.; Joseph P. Vacanti, Winchester, Mass.

[73] Assignees: Massachusetts Institute of Technology, Cambridge; Children's Hospital, Boston, both of Mass.

[21] Appl. No.: 972,156

[22] Filed: Nov. 5, 1992

[51] Int. Cl.⁶ .................. C08G 63/08; C08G 69/00; C08G 69/12
[52] U.S. Cl. .................. 528/354; 424/78.19; 424/426; 424/484; 424/486; 435/180; 435/181; 435/182; 514/1; 514/2; 528/357; 528/361; 530/815
[58] Field of Search ........... 424/426, 486, 484, 78.19; 435/180, 181, 182; 528/271, 354, 357, 361; 530/815; 514/1, 2

[56] References Cited

U.S. PATENT DOCUMENTS

| | | | |
|---|---|---|---|
| 2,668,162 | 2/1954 | Lowe | 528/357 |
| 2,676,945 | 4/1954 | Higgins | 525/710 |
| 3,839,297 | 10/1974 | Wasserman et al. | 528/357 |
| 4,048,256 | 9/1977 | Casey et al. | 525/444 |
| 4,673,566 | 6/1987 | Goosen et al. | 435/180 |

(List continued on next page.)

FOREIGN PATENT DOCUMENTS

| | | |
|---|---|---|
| 0086613 | 8/1983 | European Pat. Off. |
| WO92/15676 | 9/1992 | WIPO |
| 93/10655 | 11/1994 | WIPO |

OTHER PUBLICATIONS

Bumgardner, G. I., Fasola, C. and Sutherland D. F. R., "Prospects for Hepatocyte Transplantation," *Hepatology*, vol. 8, pp. 1158–1161 (1988).

Cima, L., Ingber, D., Vacanti, J., and Langer, R. "Hepatocyte Culture on Biodegradable Polymeric Substrates," *Biotech. Bioeng.*, vol. 38, pp. 145–158 (1991).

Cima, L., et al., "Tissue Engineering by Cell Transplantation Using Degradable Polymer Substrates," *J. Biomech. Eng.*, vol. 113, pp. 143–151 (1991).

Craig, P. H., et al., "A Biologic Comparison of Polyglactin 910 and Polyglycolic Acid Synthetic Absorbable Sutures," *Surgery*, vol. 141, pp. 1–10 (1975).

Dawson, R. M., Broughton, R. L., Stevenson, W. T. K. and Sefton, M. V., "Microencapsulation of CHO Cells in a Hydroxyethyl Methacrylate-Methyl Methacrylate Copolymer," *Biomaterials*, vol. 8, pp. 360–366 (1987).

Frazza, E. J. and Schmitt, E. E., "A New Absorbable Suture," *J. Biomed. Mater. Res. Symposium*, vol. 1, pp. 43–58 (1971).

Gilding, D. K. and Reed, A. M., "Biodegradable Polymers for Use in Surgery-Polyglycolic/Poly(lactic acid) Homo-and Co-polymers": 1, *Polymer*, vol. 20, pp. 1459–1464 (1979).

Jaffe, V., Darby, H. and Selden, C., "The Growth of Transplanted Liver Cells within the Pancreas," *Transplantation*, vol. 45, pp. 497–498 (1987).

Lim, F., "Microencapsulation of Living Cells and Tissues," *Applied Biochemistry and Biotechnology*, vol. 10, pp. 81–85 (1984).

Ricordi, C., Flye, M. W. and Lacy, P. E., "Renal Subcapsular Transplantation of Clusters of Hepatocytes in (List continued on next page.)

*Primary Examiner*—Samuel A. Acquah
*Assistant Examiner*—Shelley A. Dodson
*Attorney, Agent, or Firm*—Patrea L. Pabst

[57] ABSTRACT

Polymers more suitable for use in organ transplantation are formed by coupling biologically active moieties to the free amino groups of polymers formed by incorporation of α amino acids into polymers formed of alpha hydroxy acids such as lactic acids. In the preferred embodiment, the peptides are coupled to the free amino groups.

23 Claims, 6 Drawing Sheets

U.S. PATENT DOCUMENTS

| | | | |
|---|---|---|---|
| 4,689,293 | 8/1987 | Goosen et al. | 424/424 |
| 4,696,286 | 9/1987 | Cochrum | 435/182 |
| 4,806,355 | 2/1989 | Goosen et al. | 424/424 |
| 5,010,167 | 4/1991 | Ron et al. | 528/328 |
| 5,248,761 | 9/1993 | Hermes | 528/361 |

OTHER PUBLICATIONS

Conjunction with Pancreatic Islets," *Transplantation,* vol. 45, pp. 1148–1151 (1987).

Sun, A. M., O'Shea, G. M. and Goosen, M. F. A., "Injectable Microencapsulated Islet Cells as a Bioartificial Pancreas," *Applied Biochemistry and Biotechnology,* vol. 10, pp. 87–89 (1984).

Sun, A. M., et al., "Microencapsulated Hepatocytes: An *in Vitro* and *in Vivo* Study," *Biomat. Art. Cells. Art. Org.,* vol. 15, pp. 483–496 (1987).

Vacanti, J. P., "Beyond Transplantation, Third Annual Samuel Jason Mixter Lecture," *Archives of Surgery,* vol. 123, pp. 545–549 (1988).

Wong, H. and Chang, T. M. S., "The Viability and Regeneration of Artificial Cell Microencapsulated Rat Hepatocyte Xenograft Transplants in Mice," *Biomat., Art. Cells, Art. Org.,* vol. 16, pp. 731–739 (1988).

Brode, G. L. and Koleske, J. V., "Lactone Polymerization and Polymer Properties," *J. Macromol. Sci. Chem.,* vol. A6, pp. 1109–1144 (1972).

Cowsar, D., Tice, T. R., Gilley, R. M. and English, J. P., "[8]Poly(lactide-co-glycolide) Microcapsules for Controlled Release of Steroids," *Methods in Enzymology,* vol. 112, pp. 101–116 (1985).

D'Souza, S. E., Ginsberg, M. H., Lam, S. C. T. and Plow, E. F., "Chemical Cross–Linking of Arginyl–Glycyl–Aspartic Acid Peptides to an Adhesion Receptor on Platelets," *The Journal of Biological Chemistry,* vol. 263, pp. 3943–3951 (1988).

Dunsing, R. and Kricheldorf, H. R., "Polylactones; 5, Polymerization of L,L–Lactide by Means of Magnesium Salts," *Polymer Bulletin,* vol. 14, pp. 491–495 (1985).

Gilding, D. K., Reed, A. M. and Askill, I. N., "Calibration in Gel Permeation Chromatography: Primary, Universal and Empirical Methods," *Polymer,* vol. 22, pp. 505–512 (1981).

Greene, T. W., "Protective Groups in Organic Synthesis," pp. 239–241, John Wiley and Sons, Inc., New York (1981), Greenstein, J. P. and Winitz, M., Chemistry of the Amino Acids, vol. 2, pp. 887–901, John Wiley and Sons, Inc., New York (1961).

Helder, J. et al., "Synthesis of Poly [Oxyethylidenecarbonylimino–(2–Oxoethylene)][Poly(Glycine–D,L–Lactic Acid)]by Ring Opening Polymerization," *Markromol. Chem., Rapd Commun.,* vol. 6, pp. 9–14 (1985).

Helder, J., and Feiien, J., "Copolymers of D,L–Lactic Acid and Glycine," *Makrom. Chem. Rapid Commun.,* vol. 7, pp. 193–198 (1986).

Hoare, D. G. and Koshland, D. E. Jr., "A Method for the Quantitative Modification and Estimation of Carboxylic Acid Groups in Proteins," *J. Biol. Chem.,* vol. 242, pp. 2447–2453 (1967).

Ivin, J. K. and Saegusa, T., eds., "Ring Opening Polymerization," vol.s 1–3, Elseveir Applied Science Publishers, New York (1984).

Kohn, F. E., Ommen, J. G. van and Feijen, J., "The Mechanism of the Ring–Opening Polymerization of Lactide and Glycolide," *Eur. Polym. J.,* vol. 19, pp. 1081–1088 (1983).

Kohn, F. E., Van Den Berg, J. W. A., and Van De Ridder, G., "The Ring–Opening Polymerization of D,L–Lactide in the Melt Initiated with Tetraphenyltin," *J. Applied Polymer Sci.,* vol. 29, pp. 4265–4277 (1984).

Kricheldorf, H. R., Jonte, J. M. and Berl, M., "Polylactones: 3, Copolymerization of Glycolide with L,L–Lactide and other Lactones," *Makromol. Chem. Suppl.,* vol. 12, pp. 25–38 (1985).

Kricheldorf, H. R. and Sumbel, M., "Polylactones–18, Polymerization of L,L–Lactide with Sn(II) and Sn(IV) Halogenides," *Eur. Polym. J.,* vol. 25, pp. 585–591 (1989).

Leenslag, J. W. and Pennings, A. J., "Synthesis of High Molecular Weight Poly(L–Lactide) Initiated with Tin 2–Ethylhexanoate," *Makromol. Chem.,* vol. 188, pp. 1809–1814 (1987).

Mooney, D., et al., "Switching Between Growth and Differential in Hepatocytes: Control by Extracellular Matrix," *J. Cell. Biol.,* Thirteenth Annual Meeting, abstracts, pp. 816.

Naravanan, S., et al., "Glutaraldehyde–P, a Stable, Re- (List continued on next page.)

OTHER PUBLICATIONS active Aldehyde Matrix for Affinity Chromatography," *Analytical Biochemistry*, vol. 188, pp. 278–284 (1990).

Samyn, C. and Van Beylan, M., "Polydepsipeptides: Ring-Opening Polymerization of 3-Methyl-2,5-Morpholinedione, 3,6-Dimethyl-2,5-Morpholinedione and Copolymerization Thereof With D,L-Lactide," *Makromol. Chem., Macromol Symp.*, 19, 225–234 (1988).

Sawan, S. P. and Barry, J. J., "Quantitation of Poly (d,I-Lactic Acid) Degradation Products by HPLC," *Polymer Preprints*, vol. 29, pp. 299–300 (1988).

Sheehan, J. C., Preston, J., and Cruickshank, P. A., "A Rapid Synthesis of Oligopeptide Derivatives Without Isolation of Intermediates," *J. Am. Chem. Soc.*, vol. 87, pp. 2492–2493 (1965).

Staros, J. V., "H-Hydroxysulfosuccinimide Active Esters: Bis(N-hydroxysulfosuccinimide) Esters of Two Dicarboxylic Acids are Hydrophilic, Membrane-Impermeant, Protein Cross-Linkers," *Biochemistry*, vol. 21, pp. 3950–3955 (1982).

Veld, P. J. A. int, et al., "Synthesis of Alternating Polydepsipeptides by Ring-Opening Polymerization of Morpholine-2,5-Dione Derivatives," *Makromol. Chem.*, vol. 191, 1813–1825 (1990).

Weston, P. D. and Avrameas, S., "Proteins Coupled to Polyacrylamide Beads Using Glutaraldehyde," *Biochem. and Biophys. Research Comm.*, vol. 45, pp. 1574–1580 (1971).

Yamada, H., et al., "Cyclic Peptides: VIII, Synthesis and Tryptic Hydrolysis of Cyclic Depsidipeptides Containing a Lysine Residue," *Int. J. Peptide Protein Res.*, vol. 16, pp. 61–65 (1980).

Yasutake, A., et al., "Cyclic Peptides: VIII. Synthesis and Tryptic Hydrolysis of Cyclic Depsidipeptides Containing a Lysine Residue,"0 *Int. J. Peptide Protein Res.*, vol. 16, pp. 61–65 (1980).

Yonezawa, N., Toda, F. and Hasegawa, M., "Synthesis of Polydepsipeptides: Ring-opening Polymerization of 6-Isopropylmorphiline-2,5-dione and 6-Isopropyl-4-Methylmorpholine-2,5- dione," *Makromol. Chem., Rapid Commun.*, vol. 6, pp. 607–611 (1985).

Arnold, S., and Lenz, R., "Synthesis of Stereoregular Poly(alkyl Malolactonates)," *Makromol. Chem. Macromol. Symp.* vol. 6, pp. 285–303 (1986).

Barrera, D. et al., "Poly (lactic acid–co–Lysine); A new material for organ regeneration," AIChE Abstract (Nov. 18, 1991).

Boustta, M., et al., "New Functional Polyamides Derived from Citric Acid and L-Lysine: Synthesis and Characterization," *Makromol. Chem., Macromol. Symp.* vol. 47, pp. 345–355 (1991).

Brandley, B., Shaper, J., and Schnaar, R., "Tumor Cell Haptotaxis on Immobilized N-Acetylglucosamine Gradients," *Developmental Biology*, vol. 140, pp. 161–171 (1990).

Brandley, B., et al., "Covalent Attachment of an Arg--Gly-Asp Sequence Peptide to Derivatizable Polyacrylamide Surfaces: Support of Fibroblast Adhesion and Long-Term Growth", *Analytical Biochemistry*, vol. 172, pp. 270–278 (1988).

Braud, C., Bunel, C., and Vert, M., "Poly(beta-Malic Acid): A New Polymeric Drug Carrier," Polymer Bulletin, vol. 13, pp. 293–299 (1985).

Braud, C., et al., "Poly(beta-Malic Acid) Stereocopolymers: Structural Characteristics and Degradation in Aqueous Media," Polymer Preprints, 29:600 (1988).

Braud, C., Bunel, C., Garreau, H., and Vert, M., "Evidence for the Amphiphilic Structure of Partially Hydrogenolyzed Poly(beta-Malic Acid Benzyl Ester)," *Polymer Bulletin*, vol. 9, pp. 198–203 (1983).

Breuers, W., Klee, D., and Hocker, H., "Immobilization of a fibronectin Fragment at the Surface of a Polyurethane Film," *J. Materials Sci.: Materials in Medicine*, vol. 2, pp. 106–109 (1991).

Bruin, P., Smedinga, J., and Pennings, A., "Biodegradable Lysine Diisocyanate-based Poly(-Glycolide-co-Caprolactone)-Urethane Network in Artificial Skin," *Biomaterials*, vol. 11, p. 292 (1990).

Caron, A., Braud, C., Bunel, C., and Vert, M., "Blocky Structure of Copolymers Obtained by Pd/C-Catalyzed Hydrogenolysis of Benzyl Protecting Groups as Shown by Sequence-Selective Hydrolytic Degradation in Poly(beta-Malic Acid) Derivatives," *Polymer*, vol. 31, pp. 1797–1801 (1990).

Chadwick, A., and Pacsu, E., "The Resolution and Rates of Hydrolysis of d,l-alpha-Bromopropionic Acid (List continued on next page.)

OTHER PUBLICATIONS and its Glycine Derivatives," vol. 65, pp. 392-401 (1943).

Cole, C. A., et al., "Isopropylacrylamide (NIPAAM) and N-Acryloxysuccinimide (NASI) Copolymer: A Water-Soluble, Activated Polymer for Protein Conjugation," *Polymer Preprints,* vol. 27, No. 1, p. 237 (1986).

Domb, A., etal., "Biodegradable Polymers Derived from Amino Acids, *Biomaterials,* vol. II, pp. 686-688 (1990).

Domb, A., et al., "The Formation of Propylene Fumarate Oligomers for Use in Bioerodible Bone Cement Composites," *J. Polymer Sci., Part A: Polymer Chemistry,* vol. 28, pp. 973-985 (1990).

Everaerts, A., Samyn, C., and Smets, G., "Tailor Made Partially Substituted Poly(iminoethylene) and Derivatives in Activated Ester Hydrolysis, *Makromol. Chem.,* vol. 185, pp. 1897-1904 (1984).

Ferruti, P., and Ranucci, E., "New Functional Polymers for Medical Applications," *Polymer Journal,* vol. 23, No. 5, pp. 541-550 (1991).

Fournie, P., and Domurado, D., "In Vivo Fate of Repeat-Unit-Radiolabeled Poly(beta-Malic Acid), a Water Soluble Biodegradable Drug Carrier," *J. Bioactive and Compatible Polymers,* vol. 5, pp. 381-395 (1990).

Fournie, P., and Domurado, D., "In Vivo Fate of Repeat-Unit-Radiolabeled Poly(beta-Malic Acid), a Potential Drug Carrier," *J. Bioactive and Compatible Polymers,* vol. 7, pp. 113-129 (1992).

Gelbin, M., and Kohn, J., "Synthesis and Polymerization of N-Z-L-Serine-Beta-Lactone and Serine Hydroxybenzotriazole Active Esters," *J.A.C.S.,* vol. 114, pp. 3962-3965 (1992).

Goren, H. J., et al., Poly(L-lysyl-L-Alanyl-α-Glutamic Acid). I. Synthesis, Biopolymers, vol. 16, pp. 1513-1525 (1977).

Gross, R., et al., "The Polymerization of β-Monosubstituted-β-Propiolactones Using Trialkylaluminum-Water Catalytic Systems," *Polymer Preprints,* vol. 28, No. 2, (1987).

Guerin, P., et al., "Optically Active Poly(Beta-Malic Acid), *Polymer Bulletin,* vol. 14, pp. 187-192 (1985).

Helder, J., et al., "Synthesis of Polydepsipeptides by Ring Opening Polymerization," *Biological and Biomechanical Performance of Biomaterials,* pp. 245 (1986).

Hirano, Y., Hayashi, T., Goto, K., and Nakajima, A., "Synehesis and Evaluation of Oligopeptide RGDS Exhibiting Cell-Attachment Activity," *Polymer Bulletin,* vol. 26, pp. 363-370 (1991).

Ito, Y., Kajihara, M., and Imanishi, Y., "Materials for Enhancing Cell Adhesion by Immobilization of Cell-Adhesive Peptide," *J. Biomedical Materials Research,* vol. 25, pp. 1325-1337 (1991).

Kataki, R., and Goodman, M., "Polydepsipeptides, 9, Synthesis of Sequential Polymers Containing Some Amino Acids Having Polar Side Chains and (S)-Lactic Acid," *Macromolecules,* vol. 15, No. 1, pp. 25-30 (1982).

Kimura, Y., Shirotani, K., Yamane, H., and Kitao, T., "Ring-Opening Polymerization of 3(S)-[Benzyloxycarbonyl)methyl-]1,4-dioxane-2,5-dione,"*Macromolecules,* vol. 21, pp. 3338-3340 (1988).

Lin, H., et al., "Synthesis of a Novel Polyurethane Copolymer Containing Covalently Attached RGD Peptide," *Journal of Biomaterials Science,* Polymer edition, (1991).

Massia, S., and Hubbell, J., "Covalently Attached GRGD on Polymer Surfaces Promotes Biospecific Adhesion of Mammalian Cells," *Biochemical Engineering, VI, Ann. N.Y. Acad. Sci.,* vol. 589, pp. 261-270 (1990).

Massia, S., and Hubbell, J., "Covalent Surface Immobilization of Arg-Gly-Asp and Tyr-lle-Gly-Ser-Arg Containing Peptides to Obtain Well-Defined Cell Adhesive Substrates," *Analytical Biochemistry,* vol. 187, pp. 292-301 (1990).

Massia, S., and Hubbell, J., "Human Endothelial Cell Interactions With Surface-Coupled Adhesion Peptides on a Nonadhesive Glass Substrate and Two Polymeric Biomaterials," *J. Biomedical Materials Research,* vol. 25, pp. 223-242 (1991).

Massia, S., and Hubbell, J., "RGD Spacing of 440 nm is Sufficient for Integrin alpha-beta-3-Mediated Fibroblast Spreading and 140 nm For Focal Contact and Stress Fiber Formation," *J. Cell Biology* (1991).

Mathias, L., et al., "Polydepsipeptides, 6. Synthesis of Sequential Polymers Containing Various Ratios of L-Alanine and L-Lactic Acid," *J.A.C.S.,* vol. 11, No. 3, pp. 534 (1978).

Matsuda, T., et al., "Development of a Novel Artificial
(List continued on next page.)

OTHER PUBLICATIONS

Matrix with Cell Adhesion Peptides for Cell Culture and Artificial and Hybrid Organs," *Trans. Am. Soc. Artif. Intern. Organs*, vol. XXXV, p. 677 (1989).

Miura, M., et al., "Application of Lost Polymer Cell Receptor Conjugates for Cell Culture on Hydrophobic Surfaces," *The 17th Annual Meeting of the Society for Biomaterials*, p. 130 (1991).

Nakajima; K., et al., "Adsorption of Plasma Proteins on Arg-Gly-Asp-Ser Peptide-Immobilized Poly(vinyl alcohol) and Ethylene-Acrylic Acid Copolymer Films," *Polymer Journal*, vol. 22, No. 11, pp. 985–990 (1990).

Nissen, D., et al., "Polydepsipeptides, 4, Synthesis of the Alternating Polydepsipeptides Poly(Ala-Lac) and Poly(Val-Lac)," *Die Makromolekulare Chemie, Suppl.*, vol. 1, pp. 23–53 (1975).

Olivieri, M., et al., "Surface Characterization of ArginylGlycylAspartic Acid (RGD) Peptide Films," *The 17th Annual Meeting of the Society for Biomaterials*, pp. 131 (1991).

Pless, D., Lee, Y., Roseman, S., and Schnaar, R., "Specific Cell Adhesion for Immobilized Glycoproteins Demonstrated Using New Reagents for Protein and Glycoprotein Immobilization," *J. Biological Chem.*, vol. 258, No. 4, pp. 2340–2349 (1983).

Santerre, J., ten Hove, P., and Brash, J., "Polyurethanes Bearing Pendant Amino Acids: Fibrinogen Adsorption and Coagulant Properties, *J. Biomedical Materials Research*, vol. 26, pp. 1003–1018 (1982).

Santerre, J., and Brash, J., "Methods for the Covalent Attachment of Potentially Bioactive Moieties to Sulfonated Polyurethanes," *Macromolecules*, vol. 24, pp. 5497–5503 (1991).

Sederel, W., Banties, A., and Feijen, J., "A Route to Anionic Hydrophilic Films of Copolymers of L-Leucine, L-Aspartic Acid and L-Aspartic Acid Esters," *Polymer*, vol. 16, p. 735 (1975).

Sidman, K., et al., "Biodegradable Implantable Sustained Release Systems Based on Glutamic Acid Copolymers," *J. Membrane Science*, vol. 7, pp. 277–291 (1980).

Taylor, N., et al., "Chimeric DNA-RNA Hammerhead Ribozomes Have enhances in Vitro Catalytic Efficiency and Increased Stability in Vivo," *Nucleic Acids Research*, vol. 20, No. 17, pp. 4559–4565 (1992).

Vacanti, J. P., et al., "Selective Cell Transplantation Using Bioabsorbable Artificial Polymers as Matrices," *J. Pediatric Surgery*, vol. 23, pp. 3–9 (1988).

Veld, P. J. int. Dijkstra, P. J. and Feijen, J. "Synthesis of biodegradable polyesteramides with pendant functional groups,"0 *Makromol. Chem.*, 193, 2713–2730 (Nov. 1992).

Vert, M., et al., "Preparation and Properties of Poly-β-Malic Acid: A Functional Polyester of Potential Biomedical Importance," Papers presented at the Joint ACS/JCS Honolulu Meeting, 20(1):608 14 611 (1979).

Yoshida, M., Asano, M., and Kumakura, M., "Sequential Polydepsipeptides as Biodegradable Carriers for Drug Delivery Systems," *J. Biomedical Materials Research*, vol. 24, pp. 1173–1184 (1980).

Yoshida M., Asano, M., and Kumakura, M., "A New Biodegradable Polydepsipeptide Consisting of (L-alanyl)-$_n$L-Lactyl Sequences (n=0,1,2 and 3)," *Makromol. Chem., Rapid Commun.*, vol. 11, pp. 337–343 (1990).

Yoshida, M., Asano, M., and Kumakura, M., "A New Temperature-Sensitive Hydrogel with Alpha-Amino Acid Groups as Side Chain of Polymer," *Eur. Polym. J.*, vol. 25, No. 12, pp. 1197–1202 (1989).

Zienty, F., Katlafsky, B., and Pierron, E., "The Reaction Product from Aspartic and Maleic Acids in Aqueous Ammoniacal Solution," vol. 31, pp. 4240–4243 (1966).

STEP 1   INTERMEDIATE

STEP 1   PRODUCT

STEP II PRODUCT

STEP III PRODUCT

STEP III PRODUCT

STEP IV INTERMEDIATE

STEP IV PRODUCT 3-(Butyl-4-Amino Benzyloxycarbonyl)-6-Benzyl-2,5-Morpholinedione D,L-Lactide    6-Methyl-2,5-Morpholinedione 3-(Butyl-4-Benzyloxycarbonyl Amino)-6-Methyl-2,5-Morpholinedione
(Lysine Containing Monomer)

BIODEGRADABLE POLYMERS FOR CELL TRANSPLANTATION

FIELD OF THE INVENTION

The present invention describes the synthesis and applications of a hydrolytically degradable polymer useful in biomedical applications involving the interaction of cells with the polymer structure.

BACKGROUND OF THE INVENTION

Over the years, there have been many successful uses of polymers in medicine. Most of these applications require minimal polymer cell interactions. Consequently, there has been a lot of work done on minimizing the interactions of these polymer systems with the cells that they come in contact with.

However, one challenge in the area of biomedical materials that has received less attention is the development of substrates that can interact favorably with mammalian cells either in vitro or in vivo. Such materials could be useful for many applications from the basic study of how cells interact with surfaces to applied areas such as in vitro mammalian cell culture for the production of useful materials and in vivo cell transplantation for replacement of lost cellular function.

To illustrate the need for in vivo cell transplantation, it is worth considering that the success of whole organ transplantation is limited by donor organ availability. As an example, transplantation of the liver is often times successful but has plateaued at about 2200 transplants per year because of donor scarcity. Unfortunately, 30,000 Americans die every year of liver disease while an additional 5 million Americans are affected. The cost to the economy is more than $14 billion dollars annually. The situation is similar with other organ systems such as the kidney, pancreas, lung, and heart.

The demand for replacement organs is therefore very high. However, since the function of most of these organs is so complex and in most cases not yet completely understood, synthetically recreating their function is practically impossible. Alternative treatments concentrate on manipulating the smallest functional unit of the organ, the individual cell. Many groups have attempted cell transplantation under a variety of conditions (Bumgardner, G. L.; Fasola, C.; and Sutherland D. E. R., "Prospects for Hepatocyte Tranplantation," *Hepatology*, 8, 1158–1161 (1988); Wong, H. and Chang, T. M. S.. "The Viability and Regeneration of Artificial Cell Microencapsulated Rat Hepatocyte Xenograft Transplants in Mice," *Biomat., Art. Cells, Art. Org.*, 16, 731–739 (1988); Vacanti, J. P.; Morse, M. A.; Saltzman, M.; Domb, A. J.; Perez-Atayde, A.; and Langer, R., "Selective Cell Transplantation Using Bioabsorbable Artificial Polymers as Matrices," *Journal of Pediatric Surgery*, 23, 3–9 (1988); U.S. Pat. No. 4,696,286 to Cochrum (1987); Dawson, R. M.; Broughton, R. L.; Stevenson, W. T. K.; and Sefton, M. V., "Microencapsulation of CHO Cells in a Hydroxyethyl Methacrylate-Methyl Methacrylate Copolymer," *Biomaterials*, 8, 360–366 (1987); Jaffe, V.; Darby, H.; and Selden, C., "The Growth of Transplanted Liver Cells within the Pancreas," *Transplantation*, 45, 497–498 (1987); Ricordi, C.; Flye, M. W.; and Lacy, P. E., "Renal Subcapsular Transplantation of Clusters of Hepatocytes in Conjunction with Pancreatic Islets," *Transplantation*, 45, 1148–1151 (1987); Sun, A. M.; Cai, Z.; Shi, Z.; Ma, F.; and O'Shea, G. M., "Microencapsulated Hepatocytes: An in vitro and in vivo Study," *Biomat., Art. Cells, Art. Org.*, 15, 483–496 (1987); Sun, A. M.; O'Shea, G. M.; and Goosen, M. F. A., "Injectable Microencapsulated Islet Cells as a Bioartificial Pancreas," *Applied Biochemistry and Biotechnology*, 10, 87–99 (1984); Lim, F., "Microencapsulation of Living Cells and Tissues," *Applied Biochemistry and Biotechnology*, 10, 81–85 (1984)). When suspensions of cells have been injected, only small numbers survived. In addition, the cells that did survive had inadequate three dimensional structure and no way to form an appropriate structure. Some researchers have encapsulated cells, and this procedure provides excellent protection from the host's immune system. Often times, however, the barrier is too large and does not allow for sufficient exchange between the vascular supply and the cells. Moreover, the body sometimes forms a fibrous capsule around the implant which creates an additional barrier to the flow of nutrients. These approaches have had varying levels of success, but none has yet produced a viable clinical solution to the need for organs for transplantation.

Clinical success in the area of cell transplantation depends on efficiently using the available donor material and providing an environment conducive to long-term cell survival, differentiation and growth. One promising approach is to attach isolated cells and cell clusters onto synthetic biodegradable polymer scaffolds in vitro and then to implant the polymer-cell scaffold into recipients thereby replacing whole organ function with this device (Vacanti, J. P. "Beyond Transplantation, Third Annual Samuel Jason Mixter Lecture," *Archives of Surgery*, 123, 545–549 (1988)). With this approach, several implants could be obtained from each donor organ or cell material obtained from living donors. This could also help eliminate the need for immunosuppressive therapy, which is often required following organ transplantation.

The key to the success of this cell transplantation technique is in the design of the synthetic polymer scaffold (Cima, L., Ingber, D., Vacanti, J., and Langer, R. Hepatocyte Culture on Biodegradable Polymeric Substrates, *Biotech. Bioeng.*, 38, 145–158, 1991; Cima, L.,, Vacanti, J., Vacanti, C., Ingber, D., Mooney, D., and Langer, R., "Tissue Engineering by Cell Transplantation Using Degradable Polymer Substrates," *J. Biomech. Eng.*, 113, 143–151, 1991). This scaffold has several functions. First it must provide for active polymer/cell interactions for most mammalian cells must adhere to a surface in order to survive. It is also essential that this adhesion occur in such a manner that the cells continue to function normally. If the cells survive, but do not function normally, transplanting them into a patient is futile. Next, the polymer scaffold must have suitable surface chemistry to guide and reorganize the cell mass. Finally, the three dimensional structure must be designed to deliver a significant number of cells while allowing for the proper diffusion of nutrients.

Several criteria can be used to define the ideal substrate. Biocompatibility is essential in order to prevent acute adverse tissue responses that could impair the function of the transplanted cells. Biodegradability is desired to provide a completely natural tissue replacement without the possibility of chronic tissue reaction to the foreign body. The mechanical properties must allow for easy and reproducible processing into a variety of shapes, and the resulting devices must maintain their shape once implanted. Finally, the surface chemistry must be easily manipulated so that it can be optimized to meet the needs of each application.

One possible family of matrices that is commercially available consists of the purified extracellular matrix components, such as fibronectin, laminin, and collagen. Although these matrices provide great biocompatibility and cell adhesion, they do not have sufficient mechanical properties to build a stable three dimensional structure independent of the cells. It is also difficult to obtain high quality matrix material on a consistent basis since it must be harvested from natural sources.

Another possible matrix material that is produced commercially is surgical suture material. This is made from polyglycolic acid, polylactic acid and copolymers of glycolic and lactic acid. The biocompatibility and biodegradability of these polymers are well characterized, and the physical strength and fiber forming properties are good (Gilding, D. K. and Reed, A. M., "Biodegradable Polymers for Use in Surgery—Polyglycolic/Poly(lactic acid) Homo- and Copolymers: 1, Polymer, 20, 1459–1464 (1979); U.S. Pat. No. 4,048,256 to Casey, D. J. and Epstein, M., "Normally-Solid, Bioabsorbable, Hydrolyzable, Polymeric Reaction Product," (1977); Craig, P. H.; Williams, J. A.; Davis, K. W.; Magoun, A. D.; Levy, A. J.; Bogdansky, S.; and Jones, J. P. Jr., "A biologic Comparison of Polyglactin 910 and Polyglycolic Acid Synthetic Absorbable Sutures," Surgery, 141, 1–10 (1975); Frazza, E. J. and Schmitt, E. E., "A New Absorbable Suture," J. Biomed. Mater. Res. Symposium, 1, 43–58 (1971)). Also, since these polymers are used as suture material, they have already been approved for implantation. Unfortunately, the surface of these materials cannot be easily manipulated to provide optimal surface chemistry that could meet the needs of cells for each application.

A polymer is needed that has the beneficial qualities of polylactic acid but also provides for an easily manipulated surface chemistry.

It is therefore an object of the present invention to provide a biodegradable, biocompatible polymer modified to increase cell adhesion.

It is a further object of the present invention to provide such a polymer that has the physical and mechanical properties that allow the polymer to be processed into a matrix suitable for seeding with cells and implantation into a patient using standard surgical techniques.

SUMMARY OF THE INVENTION

Polymers have been designed which degrade in vivo to non-toxic residues that have biologically active moieties such as amino acids bound to the polymer, either directly or via short side chains. In the preferred embodiments, the biologically active moieties are coupled to the polymers via free carboxylic acids, amino groups, sulfide groups, or hydroxyl groups on the amino acids. The resulting polymers have good mechanical and biological properties.

In the preferred embodiment, monomers containing amino acids with reactive side chains, such as lysine, have been synthesized which are copolymerized with the lactic acid containing monomer, lactide, the glycolic acid containing monomer, glycolide, or any other monomers with similar mechanisms of polymerization. The reactive sites on the amino acids are protected with standard protecting groups. Copolymerized with the lactide, the resulting copolymers are of the form poly (lactic acid-co-amino acid) with the amino acid being incorporated into the backbone via an amide bond. If the percentage of the amino acid subunit is low, in the range of 1–10%, the mechanical properties will not be disrupted. However, higher percentages may be desirable for certain applications, even though the mechanical properties may not be quite as good. The reactive side chains of the amino acids are made available by removing the protecting group using standard deprotection methods. These reactive side chains are now available for modification by any of the normal methods used in coupling chemistry. In the most preferred embodiment, attachment peptides are bound to the amino acids where they serve to enhance binding of cells to the polymer.

DETAILED DESCRIPTION OF THE INVENTION

Methods for synthesis of polymers having advantageous properties for implantation and cell culture are described. The polymers are characterized by biocompatibility, degradability into non-toxic products normally present in the body, preferably by hydroylsis, and the presence of accessible biologically active moieties bound to the polymers by amino acids polymerized within the polymer or chemically coupled to the polymer.

In the preferred embodiments, the polymers are formed by polymerization of α amino acids with α hydroxy acids. The biologically active moieties are then coupled to the amino acids via free carboxylic acids, amino groups, sulfide groups, or hydroxyl groups on the amino acids.

Synthesis of the Amino Acid Containing Monomer

Figure 1:
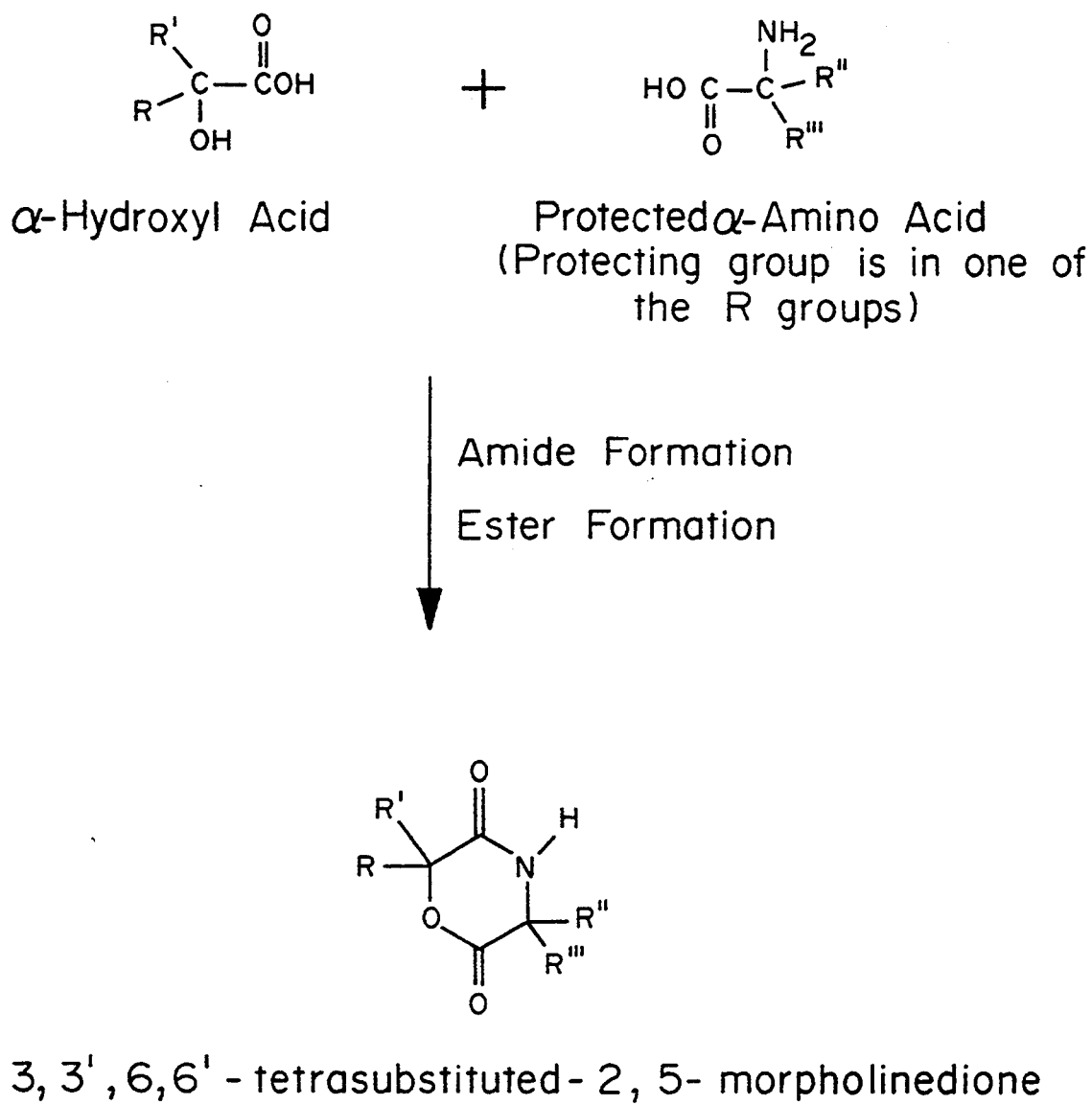
FIG. 1 is a schematic of the reaction of an α-hydroxyl acid with a protected α-amino acid to yield the cyclilized hydroxyl acid-co-amino acid..
Figure 2A:
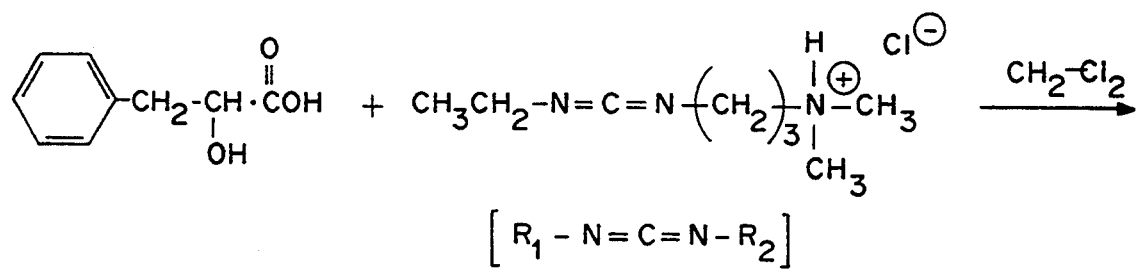
FIGS. 2A–D is a schematic of the formation of 3-(butyl-4-benzyloxycarbonyl amino)-6-benzyl-2,5-morpholinedione, where an ester bond is formed first and then the product cyclized through amide bond formation, as shown in the prior art.
Figure 2A:
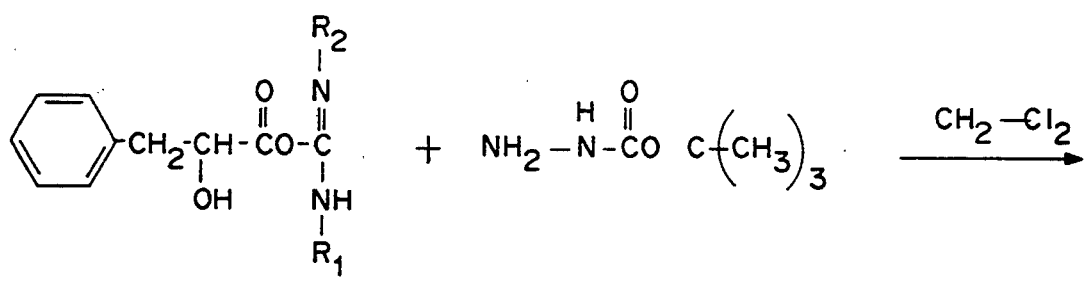
Figure 2A:
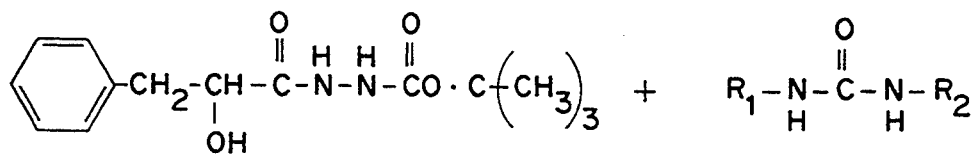
Figure 2B:
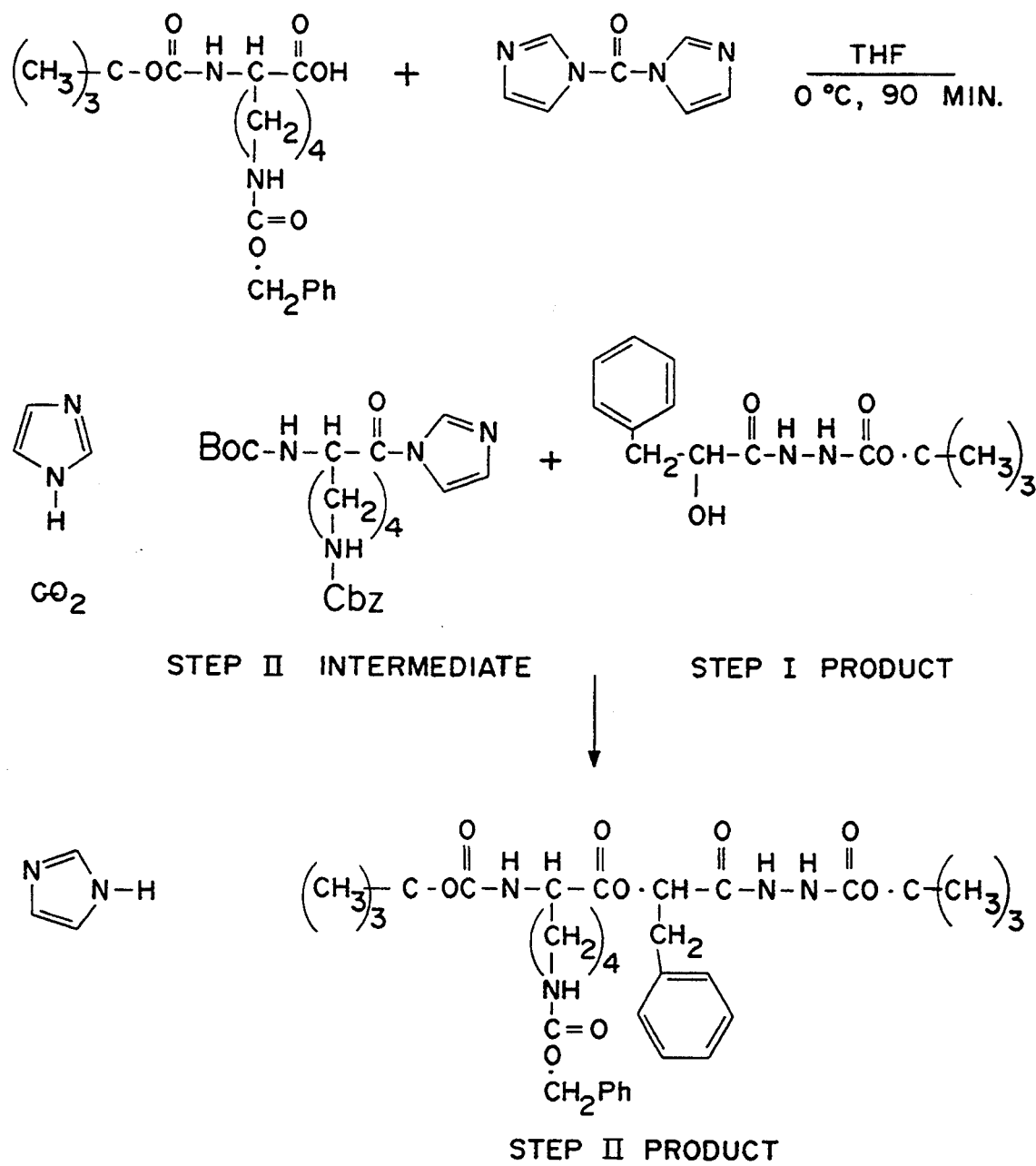
Figure 2C:
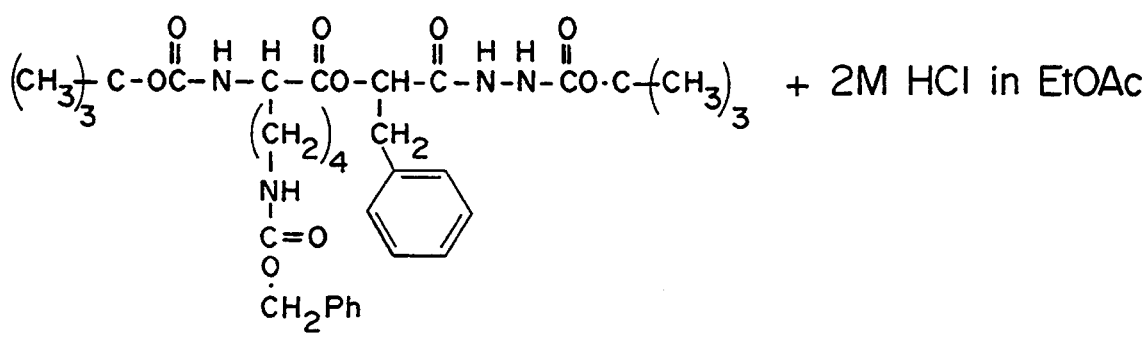
Figure 2C:
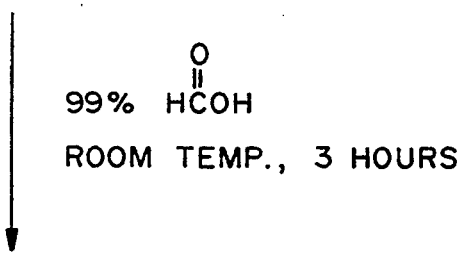
Figure 2C:
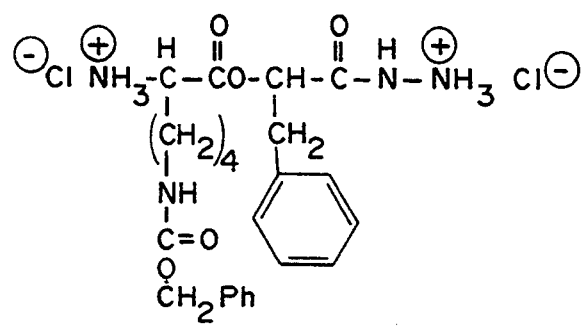
Figure 2D:
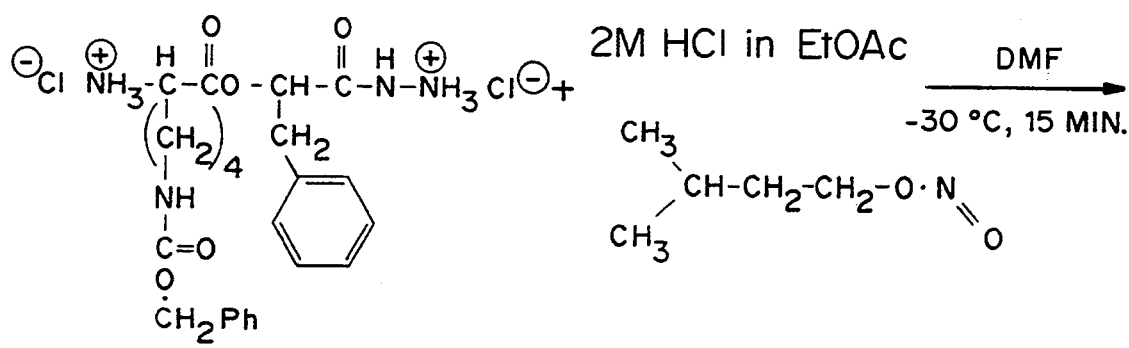
Figure 2D:
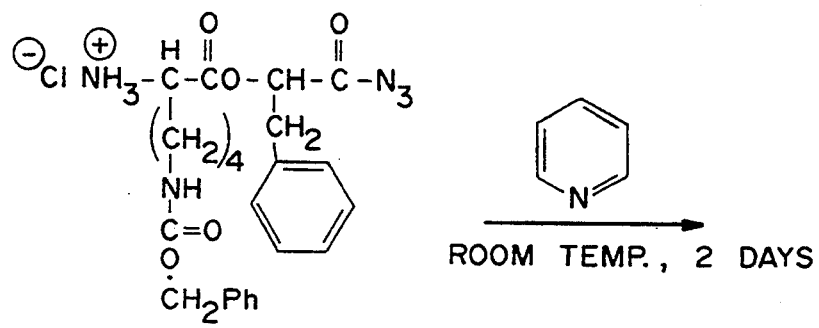
Figure 2D:
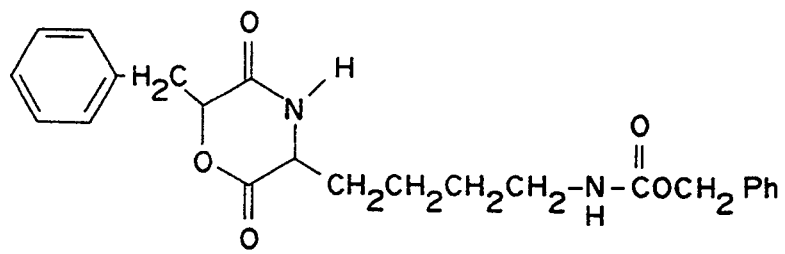

The general concept for producing the monomer in FIG. 1, referred to herein as the amino acid monomer, is to cyclize an α-hydroxy acid with an α-amino acid to yield a 3,6-disubstituted-2,5-morpholinedione.

The α amino acids are generally of the formula:

R, R'—COH—CO—OH, wherein R and R' are independently H or a linear or branched alkyl. Examples of α hydroxy acids include lactic acid and glycolic acid.

The α amino acids are preferably of the formula:

R", R'"—CNH$_2$—CO—OH, wherein R" and R'" are independently H or a linear or branched alkyl; any protected primary or secondary amino group; any protected ester; any protected hydroxyl; any protected sulfide; any protected amide; any protected guanidino; or any protected imidazole. All 20 of the common amino acids can be used. The most preferred amino acids are protected lysine and protected aspartic acid.

This transformation involves producing an amide bond and an ester bond. All synthetic routes are variations of two main themes: 1) formation of the ester bond and then cyclization via amide bond formation or 2) formation of the amide bond and then cyclization via ester bond formation.

Several standard reactions are used to form amide bonds. In general, these reactions consist of activating the carboxylic acids to facilitate nucleophilic attack. Table I shows a broad sample of activated carboxylic acids (Bodanszky, 1988) Bodanszky, M., *Peptide Synthesis,* Chapter V, Springer-Verlag, 1988. Each of these has its own advantages, such as side reactions, and disadvantages, such as mild reaction conditions or water solubility.

TABLE I
Activated Carboxylic Acids

R—C(=O)—Cl   Acid Chloride

R—C(=O)—N=N=N   Acid Azide

R—C(=O)—O—C(=NR')—NH—R   O-Acyl-Isourea

R—C(=O)—O—C(=O)—R   Anhydride

R—C(=O)—N(pyrrole)   N-Acyl Intermediate

R—C(=O)—O—N(benzotriazole)   1-Hydroxybenzotriazole Ester

R—C(=O)—O—N(succinimide)   N-Hydroxysuccinimde Ester

R—C(=O)—O—(C$_6$Cl$_5$)   Pentachlorophenyl Esters

Ester bond formation is more difficult in general and requires more sophisticated methods. Not only is the carboxylic acid activated but catalysts such as 4-dimethylaminopyridine are also used. It is important to note that during the formation of the first bond, either the ester or amide, the other reactive species must be protected. Table II (Bodanszky, 1988) Bodanszky, M., *Peptide Synthesis,* Chapter V, Springer-Verlag, 1988 provides a list of the more common protecting groups, which can also be referred to as blocking groups, along with the deprotecting conditions.

TABLE II

| Blocking Groups | Deblocking Conditions |
|---|---|
| Amine Blocking Groups | |
| $(CH_3)_3C$—O—C(=O)— | Mild Acid |
| (C$_6$H$_5$)—CH$_2$—O—C(=O)— | Strong Acid; H$_2$/Pd |
| (fluorenyl)CH$_2$—O—C(=O)— | Mild Base |
| Carboxylic Acid Blocking Group | |
| RO— | Mild Acid; Mild Base; H$_2$/Pd |

Two methods are applicable to the synthesis of the amino acid monomer. The first method, describing the formation of 3-(butyl-4-benzyloxycarbonyl amino)-6-benzyl-2,5-morpholinedione, is by Yasutake, A.; Miyazaki, K.; Aoyagi, H.; Kato, T.; and Izumiya, N., "Cyclic Peptides: VIII. Synthesis and Tryptic Hydrolysis of Cyclic Depsidipeptides Containing a Lysine Residue," *Int. J. Peptide Protein Res.,* 16, 61–65 (1980). An ester bond is formed first and then the product cyclized through amide bond formation. The synthetic pathway used is shown in FIG. 2. In this synthesis, one carboxyl is protected as an acyl hydrazide which is a "masked" form of the activated acyl azide. First, the ester bond is formed between the 2-hydroxy-3-phenylpropanoic acid hydroxyl group and the lysine carboxylic acid using N-hydroxy succinimide ester activation. The lysine α-amino group is then deprotected. Next, the lactic acid hydrazide is converted to the acyl azide. Finally, the cyclization is completed through amide bond formation.

Figure 3:
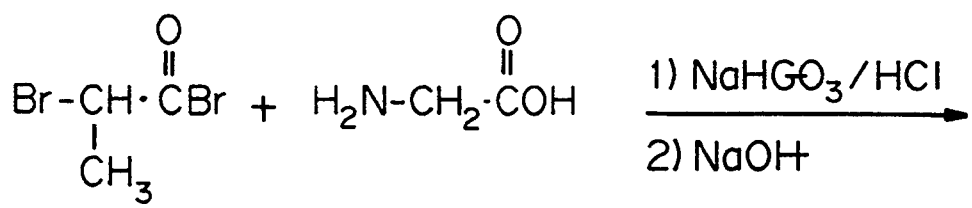
FIG. 3 is a schematic of the cyclizing of the α-hydroxy acid with an α-amino acid to make alkyl substituted 2,5-morpholinediones, where an α-bromo acyl bromide is utilized as the α-hydroxy acid equivalent, as shown in the prior art.
Figure 3:
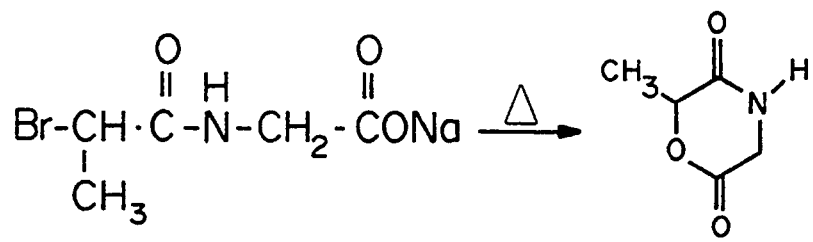

A second approach to cyclizing the α-hydroxy acid with the α-amino acid is shown in FIG. 3. This pathway is used to make alkyl substituted 2,5-morpholinediones (Samyn, C. and Van Beylen, M., "Polydepsipeptides: Ring-Opening Polymerization of 3-Methyl-2,5-Morpholinedione, 3,6-Dimethyl-2,5-Morpholinedione and Copolymerization thereof with D,L-Lactide," *Makromol. Chem., Macromol. Symp.,* 19, 225–234 (1988); Helder, J.; Kohn, F. E.; Sato, S.; van den Berg, J. W.; and Feijen, J., "Synthesis of Poly [Oxyehylidenecarbonylimino-(2-Oxoethylene)] [Poly(Glycine-D,L-Lactic Acid)] by Ring Opening Polymerization," *Makromol. Chem., Rapid Commun.,* 6, 9–14 (1985); Greenstein, J. P. and Winitz, M., *Chemistry of the Amino Acids,* Vol. 2, p 887–901, John Wiley and Sons, Inc., New York, 1961). An α-bromo acyl bromide is utilized as the α-hydroxy acid equivalent. The amide bond is formed by the general method discussed above. The cyclization through the ester bond formation takes place by an SN$_2$ displacement of the bromide with the sodium salt of the carboxylic acid. This reaction exchanges the roles of the two centers. The carboxylic acid group acts as the nucleophile, while the α-bromo group provides the electrophilic center.

Polymerization

The monomers are polymerized using a technique such as melt condensation, as exemplified using polyglycolic acid and polylactic acid.

Historically, polyglycolic acid was first produced by condensation polymerization of hydroxy acetic acid (Higgins, 1954 and Beck, 1952). However, there are many problems associated with condensation polymerizations, including long reaction times to obtain even moderate molecular weight products, side reactions which create the necessity for by-product removal, and a lack of end group control (Brode, G. L. and Koleske, J. V., "Lactone Polymerization and Polymer Properties," *J Macromol Sci.-Chem.*, A6, 1109–1144 (1972)).

In 1954 Lowe (8.Lowe, C. E., "Preparation of High Molecular Weight Polyhydroxyacetic Ester," U.S. Pat. No. 2,668,162 (1954) modified the reaction conditions of the polycondensation to obtain high yields of glycolide. This product was then purified and found to polymerize by a ring-opening mechanism to very high molecular weights using antimony trioxides or antimony trihalides. Other catalyst that have been used include: tributyltin methoxide, dibutyltin dimethoxide, dibutyltin diacetate, debutyltin oxide, dibutyltin dichloride, tin dioxide, tin dibromide, tin dichloride, tin tetrabromide, tin tetrachloride, tetraphenyl tin, lead oxide, zinc oxide, zinc, antimony trioxide, triethyl aluminum, aluminum bromide, triisobutyl aluminum, triisopropyl aluminum, magnesium acetate, magnesium stearate, magnesium 2,4-pentanedionate, magnesium ethoxide, magnesium oxide, and stannous octoate, with stannous octoate being the preferred catalyst (Gilding, D. K.; Reed, A. M.; and Askill, I. N., "Calibration in Gel Permeation Chromatography: Primary, Universal and Empirical Methods," *Polymer* 22, 505–512 (1981).; U.S. Pat. No. 3,839,297 to Wasserman, D. and Versfeit, C. C., "Use of Stannous Octoate Catalyst in the Manufacture of L(-)Lactide-Glycolide Copolymer Sutures," (1974); Frazza, 1971; Higgins, N. A., "Condensation Polymers of Hydroxyacetic Acid," U.S. Pat. No. 2,676,945 (1954); Kohn, F. E.; Ommen, J. G. van; and Feijen, J., "The Mechanism of the Ring-Opening Polymerization of Lactide and Glycolide," *Eur. Polym. J.*, 19, 1081–1088 (1983); Kohn, F. E.; Van Den Berg, J. W. A.; and Van De Ridder, G., "The Ring-Opening Polymerization of D,L-Lactide in the Melt Initiated with Tetraphenyltin," *Journal of Applied Polymer Science*, 29, 4265–4277 (1984); Cowsar, R. D.; Tice, T. R.; Gilley, R. M.; and English, J. P., "[8] Poly (lactide-co-glycolide) Microcapsules for Controlled Release of Steroids," *Methods in Enzymology*, 112, 101–116 (1985); Dunsing, R and Kricheldorf, H. R., "Polylactones: 5. Polymerization of L,L-Lactide by Means of Magnesium Salts," *Polymer Bulletin*, 14, 491–495 (1985); Sawan, S. P. and Barry, J. J., "Quantitation of Poly (d,l-Lactic Acid) Degradation Products by HPLC," *Polymer Preprints*, 29, 299–300 (1988); Kricheldorf, H. R.; Jonte, J. M.; and Berl, M., "Polylactones: 3. Copolymerization of Glycolide with L,L-Lactide and other Lactones," *Makromol. Chem., Suppl.*, 12, 25–38 (1985); Kricheldorf, H. R. and Sumbel, M., "Polylactones—18. Polymerization of L,L-Lactide with Sn(II) and Sn(IV) Halogenides," *Eur. Polym. J.*, 25, 585–591 (1989).). The mechanism of the ring-opening polymerization of glycoside and lactide with stannous octoate is still under debate, but a nonionic insertion mechanism has gained the most acceptance (Kohn, 1984; Leenslag, J. W. and Pennings, A. J., "Synthesis of High Molecular Weight Poly(L-Lactide) Initiated with Tin 2-Ethylhexanoate," *Makromol. Chem.*, 188, 1809–1814 (1987); Kricheldorf, 1989).

Copolymerization with 2,5-Morpholinedione.

Figure 4:
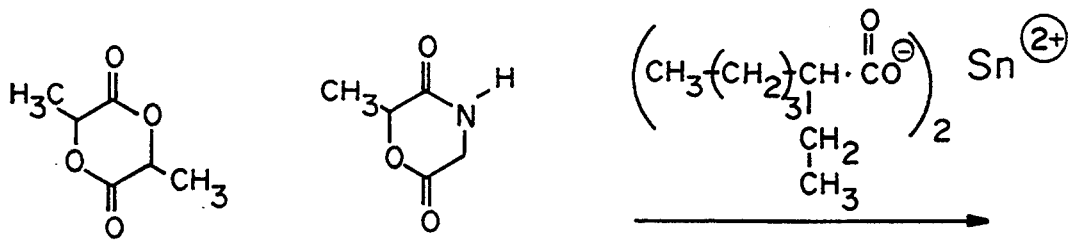
FIG. 4 is a schematic of a ring opening polymerization for lactic acid, as shown in the prior art.
Figure 4:
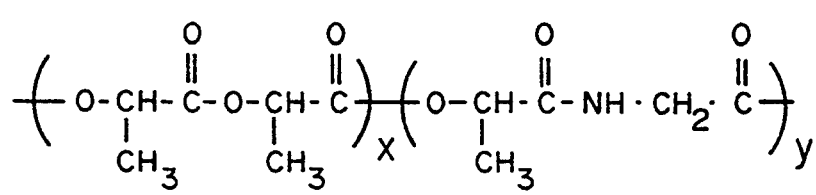

Recently, there has been an attempt to incorporate amino acid units into the backbone of polylactic acid in order to expand the range of properties available from this bioabsorbable material (Veld, P. J. A. in 't; Dijkstra, P. J.; Lochem, J. H. van; and Feijen, J., "Synthesis of Alternating Polydepsipeptides by Ring-Opening Polymerization of Morpholine-2,5-Dione Derivatives," *Makromol Chem.*, 191, 1813–1825 (1990); Samyn 1988; Helder, J. and Feijen, J., "Copolymer of D,L-Lactic Acid and Glycine," *Makromol Chem., Rapid Commun.*, 7, 193–198 (1986); Yonezawa, N.; Toda, F.; and Hasegawa, M., "Synthesis of Polydepsipeptides: Ring-opening Polymerization of 6-Isopropylmorphiline-2,5-dione and 6-Isopropyl-4-Methylmorpholine-2,5-dione," *Makromol Chem., Rapid Commun.*, 6, 607–611 (1985)). The accepted way to insert the α-amino acids into the backbone is to dimerize them with an α-hydroxy acid, such as lactic acid. This step creates a substituted morpholinedione which can be used in subsequent copolymerizations. An example of this type of copolymerization is shown in FIG. 4. Only amino acids with alkyl substituents have been copolymerized in this manner.

The substituted morpholinedione contains both an amide bond and an ester bond in the ring. Both of these functional groups could polymerize by a ring opening mechanism using several different types of initiators such as cationic, active hydrogen, anionic, and coordination (Ivin, J. K. and Saegusa, T., eds., *Ring Opening Polymerization*, Volumes 1–3, Elseveir Applied Science Publishers, New York, 1984). However, 6-member ring lactams do not polymerize under cationic or active hydrogen initiator conditions. If these conditions are used, the morpholinedione should polymerize through the ester bond.

It is expected that this ester bond will have a reactivity very similar to the reactivity of the ester bonds in lactide, due to the fact that the amide structure with its partial double bond character will increase the ring strain. Copolymerizations with lactide and methyl substituted morpholinediones at monomer ratios of 1:1 yielded polymers with a mole ratio of monomer units of 1:1 within experimental error (Samyn 1988; Helder, 1986; Yonezawa, 1985). Samyn, C. and Van Beylen, M., "Polydepsipeptides: Ring-Opening Polymerization of 3-Methyl-2,5-Morpholinedione, 3,6-Dimethyl-2,5-Morpholinedione and Copolymerization thereof with D,L-Lactide, "Makromol. Chem., Macromol. Symp., 19, 225–234 (1988); Helder, J. and Feijen, J., "Copolymer of D,L-Lactic Acid and Glycine," Makromol. Chem., Rapid Commun., 7, 193–198 (1986); Yonezawa, N.; Toda, F.; and Hasegawa, M., "Synthesis of Polydepsipeptides: Ring-opening Polymerization of 6-Isopropylmorphiline-2,5-dione and 6-Isopropyl-4-Methylmorpholine-2,5-dione," Makromol. Chem., Rapid Commun., 6, 607–611 (1985). This result suggests that the two ester bonds have similar reactivities.

Deprotection of amino groups

The removal of the amino protecting groups is essential. If this step is not completed, there will be no reactive groups available for the attachment of the biologically active moieties.

The carbonylbenzoxy amino protecting group is common in peptide synthesis, and can be cleaved by the selective method of solid phase catalytic reduction. This reaction is quite mild and should not harm the ester bonds in the backbone of the polymer. However, many other protecting groups and deprotecting conditions are available, as indicated in Table I (Greene, T. W., *Protective Groups in Organic Synthesis,* 239–241, John Wiley and Sons, Inc., New York, (1981)).

An alternative route to the deprotection is to deprotect only the surface of a polymer device that had been processed before any deprotection reactions. This method of deprotection could be completed with mildly alkaline reagents that would hydrolyze the bonds at the surface. Of course, both the ester bonds in the backbone of the polymer as well as the bonds of the protecting groups would be hydrolyzed. This surface degradation should not affect the desired mechanical properties. However, the protecting groups in the bulk of the sample would be unaffected.

Polymer Processing

The polymer can be cast into a variety of shapes by standard processing techniques, such as solvent casting and compression molding. Solvent casting is used to obtain thin films. Variables that should be considered in order to optimize this processing technique are choice of solvent, concentration of starting solution, solvent evaporation rate, casting surface, and molecular weight of the polymer. Compression molding is used to form small discs by compressing finely ground polymer powder. Variables that are important for compression molding include polymer contact surface, pressure, temperature, cooling rate if appropriate, polymer powder size, and molecular weight of the polymer.

The polymer contact surface can greatly influence the composition of the surface of the polymer film or disc. During solvent casting the polymer interfaces with air, whereas, during compression molding, the interface will probably be either metal/polymer or teflon/polymer if a teflon release tape is used. There is a concern that very hydrophobic interfaces may cause the hydrophilic amino groups to become inaccessible. The choice of solvent in solvent casting may also affect the accessibility of the amino groups.

More sophisticated processing techniques such as injection molding, fiber extrusion, fiber weaving, may be essential to obtain optimal cell function, especially in the case of hepatocytes. These methods are known to those skilled in the art.

Adhesion Moiety Attachment

Adhesion of cells to the surface of the polymer is enhanced by coupling of biologically active moieties, such as GRGDY and YIGSR (standard one letter abbreviations for amino acids are used herein, as listed in 37 C.F.R.), to the reactive side chains of the polymer such as amino groups or carboxylic acids.

Surface Activation

In the event that the reactive side chains may not be accessible to the surface of the polymer device, Several methods can be used to increase the surface reactive group accessibility. First, the surface can be exposed to an aqueous solution containing miscible hydrophilic or polar solvents such as ethanol or acetone. Such exposure should increase the flexibility of the polymer backbone by lowering $T_g$. This increased flexibility will allow the reactive groups to move to the surface while the hydrophilic nature of the aqueous solution will provide the driving force.

Another way to increase the flexibility of the polymer backbone at the surface is to expose the polymer device to solvent vapors after processing. Polar solvents should provide a greater driving force for the reactive groups to move to the surface.

Attachment Chemistry

It is important for optimal cellular function to be able to manipulate the surface chemistry of the polymer device. An important example of this is the attachment of an RGD peptide which has been shown to promote cell adhesion. The attachment of this adhesion moiety to the reactive side chains such as free amino groups on the polymer surface can be achieved by either of two methods.

The first method involves activating the C-terminus carboxylic acid of the peptide, and then reacting this group with the amino groups on the polymer surface. The C-terminus carboxylic acid can be activated by several methods as indicated in Table I. A preferred reagent is 1-ethyl-3-(3-dimethylaminopropyl)-carbodiimide (EDC) which produces an O-acyl-isourea. This activated species will react readily with free amino groups (Yamada, H.; Imoto, T.; Fujita, K.; Okazaki, K.; and Motomura, M.; "Selective Modification of Aspartic Acid-101 in Lysozyme by Carbodiimide Reaction," *Biochemistry,* 20, 4836–4842 (1981); Hoare, D. G. and Koshland, D. E. Jr., "A Method for the Quantitative Modification and Estimation of Carboxylic Acid Groups in Proteins," *The Journal of Biological Chemistry,* 242, 2447–2453 (1967); Sheehan, J. C.; Preston, J.; Cruickshank, P. A., "A Rapid Synthesis of Oligopeptide Derivatives without Isolation of Intermediates," *Journal of the American Chemical Society,* 87, 2492–2493 (1965)). However, biologically active moieties such as the RGDS peptide contain two carboxylic acid groups, one at the C-terminus and the other on the aspartic acid residue. If the C-terminus carboxylic acid is to be used to chemically attach the peptide to the polymer surface then the aspartic acid residue must be protected. A completely protected RGDS peptide can be synthesized by those skilled in the art. After attachment the peptide side chains of the peptide would have to be deprotected.

An alternative approach is to link the peptide to the polymer surface through a bifunctional molecule which is reactive towards amines at both ends. An example of such a bifunctional molecule is bis(sulfosuccinimidyl) suberate which has an N-hydroxysuccinimide ester at both ends (D'Souza, S. E.; Ginsberg, M. H.; Lam, S. C.-T.; and Plow, E. F., "Chemical Cross-Linking of Arginyl-Glycyl-Aspartic Acid Peptides to an Adhesion Receptor on Platelets," *The Journal of Biological Chemistry,* 263, 3943–3951 (1988); Staros, J. V., "N-Hydroxysulfosuccinimide Active Esters: Bis(N-hydroxysulfosuccinimide) Esters of Two Dicarboxylic Acids are Hydrophilic, Membrane-Impermeant, Protein Cross-Linkers," *Biochemistry,* 21, 3950–3955 (1982)). Another commonly used bifunctional linking reagent which reacts with amino groups is glutaraldehyde (Weston, P. D. and Avrameas, S., "Proteins Coupled to Polyacrylamide Beads Using Glutaraldehyde," *Biochemical and Biophysical Research Communications,* 45 1574–1580 (1971); arayanan, S. R.; Kakodkar, S. V.; and Crane, L. J., "'Glutaraldehyde-P', a Stable, Reactive Aldehyde Matrix for Affinity Chromatography," *Analytical Biochemistry,* 188, 278–284 (1990)). The first step in this approach is to react the polymer surface amino groups with one end of the bifunctional molecule. Next, the peptide is attached to the other end of the molecule through the N-terminus amine. It is not necessary to synthesize a protected peptide as previously mentioned, for there is only one amino group in the peptide in this example.

Bulk Attachment

Since this is a biodegradable polymer, surface modification may be insufficient. The surface layer could degrade away before performing its function. Consequently, bulk attachment strategies have also been considered. This approach also utilizes a bifunctional molecule which is reactive towards amines at both ends such as carbonyl diimidazole. This bifunctional molecule, the polymer, and the peptide can be dissolved together in a common solvent. Some side reactions may occur, which include linking of polymer-polymer and peptide-peptide, but these should not interfere excessively with the linking reaction of the polymer-peptide.

Seeding of Matrix with Cells

Cells such as hepatocytes, pancreatic cells, intestinal cells, uroendothelial cells, skin cells, muscle cells, nerve cells, and bone cells which are dissociated and viable and in a suspension are applied to a matrix formed of the polymer. Cells are provided with sufficient time to attach to the polymer, then the matrix is implanted using standard surgical techniques.

The teachings of the cited publications are indicative of the level of skill and the general knowledge of those skilled in the art. To the extent necessary, the publications are specifically incorporated herein by reference.

The present invention will be further understood by reference to the following non-limiting examples.

EXAMPLE 1

Preparation of 3-(butyl-4-benzyloxycarbonyl amino)-6-methyl-2,5-morpholinedione.

Figure 5:
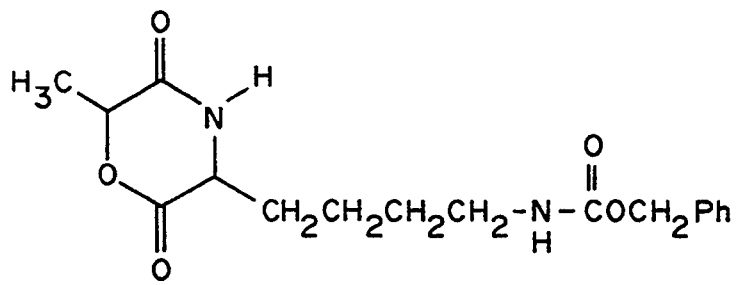
FIG. 5 is a schematic of a desired monomer structure, 3-(Butyl-4-carbonylbenzoxy amino) -6-methyl-2,5-morpholinedione, a lysine containing monomer.

This example illustrates the preparation of 3-(butyl-4-carbonylbenzoxy amino)-6-methyl-2,5-morpholinedione, a monomer containing lactic acid and lysine where the side chain amino group of lysine is protected with a carbonylbenzoxy group, as shown in FIG. 5. In the final monomer product, both the lactic acid and lysine are in the L configuration.

Weighed out:
50.0 g of D-alanine (0.56M, MW=89.09)
104.3 g of NaNO$_2$ (1.51M, MW=69.0)
700 g of Na$_2$SO$_4$ (4.93M:, MW=142.0)

Carefully add 580 ml of 48% HBr (5.19M, MW=80.9) to 2420 ml of ice water. Stir with an overhead mixer. The temperature is −10° C. Add the D-alanine and let it dissolve. Slowly add the NaNO$_2$ to the D-alanine mixture over about 20 minutes. Next, slowly add the Na$_2$SO$_4$ to the mixture over about 20 minutes. Continue to add ice to keep the mixture at −10° C. during the additions. After everything is added, continue to stir until the mixture reaches room temperature, about 1.5 hours. Decant the liquid from the remaining solids. Extract the water with ethyl ether. Dry the ethyl ether with Na$_2$SO$_4$ and then CaCl$_2$. Filter the ethyl ether and then remove the ethyl ether under vacuum. Repeat procedure up to this point. Mix the two batches. Vacuum distill using water aspirator. Collect fraction from 103°–106° C. The product is D-2-bromo propionic acid and the yield is 60%, which is 103.9 g (0.68M).

Add 70 ml (114.5 g, 0.96M) of SOCl$_2$ to the 103.9 g of D-2-bromo propionic acid. Heat to 60° C. for 7.5 hours. Collect product by vacuum distillation using a water aspirator. Collect fraction from 45°–56° C. The product is D-2-bromo propionyl chloride and the yield is 74% which is 86.3 g (0.50M). IR spectroscopy shows the typical acyl chloride peak at 1775 cm$^{-1}$ and the $^1$H NMR spectroscopy shows a quartet centered around 4.65 ppm and a doublet at 1.9 ppm.

Dilute 27.6 g (0.16M) of the D-2-bromo propionyl chloride with 200–400 ml of chloroform. Prepare a slurry of N-e-benzyloxycarbonyl-L-1 ysine (96.6 g, 0.34M) in 2000 ml dry chloroform. Add the D-2-bromo propionyl chloride solution to the slurry all at once. Let react at room temperature for 24 hours. The insoluble N-E-carbonylbenzoxy-L-lysine will react with the D-2-bromo propionyl chloride and form a soluble product and an insoluble impurity. Next, remove the solid impurity by filtration, and then remove all but 600 ml of the chloroform under vacuum. This reaction forms the amide bond between the lysine a-amino group and the lactic acid activated carboxylic acid.

Next, 24.2 ml (18.0 g, 0.14M) of diisopropyl ethyl amine is diluted in 50 ml of chloroform and then added to the chloroform mixture from the last step. This reaction mixture is then diluted with chloroform to a total of 900 ml. The reaction is heated to reflux and left to react at this temperature for 24 hours. This reaction forms a ring structure through the ester bond between the activated α-hydroxyl of lactic acid and the carboxylic acid of the lysine. Inversion occurs at the lactic acid center. Upon completion of the reaction, the chloroform is removed under vacuum. A waxy solid forms. This crude reaction product is purified by silica gel column chromatography. The eluent is 93/5/2 chloroform/methanol/acetic acid. The eluent is removed under vacuum with heating to 60° C. A viscous oil forms. The product is crystallized by washing the viscous oil with petroleum ether. A yellowish/white powder forms. This powder is recrystallized from ethyl acetate which produces a clean white powder. The yield is for these last two steps combined is 31% which is 16.6 g, 0.05M. Melting point 135°–136° C. High resolution mass spectroscopy confirmed elemental analysis; expected 334.15287 amu, experimental 334.1527 amu. The IR and NMR were also consistent.

EXAMPLE 2

Copolymerization of the monomer produced in Example-1 with lactide to make poly (lactic acid-co-N-E-carbonylbenoxy lysine).

This is an example of the copolymerization of the monomer produced in Example 1 with lactide to make poly (lactic acid-co-N-E-carbonylbenzoxy lysine).

First the polymerization flask must be siliconized to rid the glass surface of all hydroxyl groups. Throughout the polymerization procedure, all the glassware is dried in a 130° C. oven overnight and cooled under vacuum. All parts of the experiment requiring that the monomers be exposed to the atmosphere were done in a N$_2$ box.

The day before the polymerization, each of the monomers must be recrystallized from ethyl acetate in the N$_2$ box. These crystals are then dried under vacuum overnight. The monomers are then weighed out into the polymerization flask, 10.9 g lactide (75.3 mM) and 2.77 g protected lysine monomer (8.27 mM). The catalyst solution, 1.06 g of stannous octoats in 10 ml of chloroform, 0.262 mol/l, is prepared and 305 l of the catalyst solution added into the polymerization flask. The chloroform is removed under vacuum. The flask is flushed several times with argon. The flask was sealed under vacuum and transfered to 100° C. oven for 24 hours, removed from the oven and the reaction quenched in the freezer. Molecular weight before purification: Mn=72,700, Mw=72,200, Mz=88,700. The polymer was purified by dissolving in chloroform and precipitating into methanol. The yield is 80.5% which is 10.96 g. Molecular weight after purification: Mn=41,800, Mw=79,300, Mz=141,700. Transesterification occurred during the time that the polymer was dissolved which broadened the molecular weight distribution. The protected lysine content was analyzed by standard amino acid analysis and $H^1$ NMR. Both of these techniques indicate a lysine content of 2% where the maximum is 5%. DSC analysis yields Tm=158.0° C. and Tg=55.1° C.

EXAMPLE 3

Removal of the N-E-carbonylbenzoxy protecting group from the side chain of lysine.

This is an example of removing the N-E-carbonylbenzoxy protecting group from the side chain of lysine.

All the glassware was dried overnight in a 130° C. oven and cooled under argon. To the reaction vessel was added 225 ml $SiEt_3H$ (1.4M), 9.9 g of the copolymer from example 2, 225 ml methylene chloride, 1.8 g $PdCl_2$ (0.010M), and 2.1 ml $NEt_3$ (0.016M) in the order listed. The reaction was stirred at room temperature for five days. The catalyst, $PdCl_2$, was removed by filtration. 150 ml of methanol was added and let stand 10 minutes, then the solution dumped into excess methanol, approximately 3000 ml. Let stand 30 minutes, and then the precipitate collected by vacuum filtration. The polymer was dried under vacuum. The product from this reaction is poly (lactic acid-co-lysine). The yield is 79% which is 7.8 g. The molecular weights are: Mn=31,500, Mw=44,100, Mz=69,700. Proton NMR indicates that 75% of the protecting residues were removed while amino acid analysis indicates that 88% of the lysine units remain in the polymer. The IR spectrum was consistent and DSC analysis shows two melting peaks with the onset of the more intense peak at Tm=159.2° C. and Tg=55.7° C.

EXAMPLE 4

Processing of the copolymer synthesized in Example 3.

This example illustrates the processibility of the copolymer synthesized in example 3.

Solvent Casting: Poly (lactic acid-co-lysine) from Example 3 (100 mg) was weighed out into a standard 10 ml glass beaker. Chloroform (2 ml) was added to dissolve the polymer. The chloroform was allowed to evaporate very slowly over a 48 hour period. In order to remove the film from the beaker it was submersed in water for 4 hours. The free standing film is easily handled without breaking and can be cut with a razor blade or scissors. Its appearance is translucent.

Compression Molding: Poly (lactic acid-co-lysine) from Example 3 is ground to a fine powder. The powder (150 mg) is put into a die (1.4 cm diameter) and compressed at 10,000 psi for 30 minutes while the top and bottom compression plates are at 100° C. This type of film can be easily handled, but higher temperatures are necessary to obtain a translucent film. Higher temperatures also cause the film to become brittle.

EXAMPLE 5

The hydrolytic degradation of the poly (lactic acid-co-lysine).

This example illustrates the hydrolytic degradation of the poly (lactic acid-co-lysine) described in example 3.

The solvent cast films of poly (lactic acid-co-lysine) from Example 4 were immersed in PBS pH 7.2 at 37° C. with rotational agitation at 120 rpm. The buffer was changed weekly and the films were sacrificed at various time points. These films degrade more quickly than homopolymers of lactic acid. By five weeks, the Mw of the copolymer was half of its original value and the films had lost integrity, breaking up into many pieces. The remaining weight of the films decreased gradually. By 23 weeks more than 40% of the weight was lost. Lactic acid was also released into the buffer, as determined by an enzymatic assay.

EXAMPLE 6

Bulk attachment of GRGDY-peptide into polymer synthesized in Example 3

This is an example of the attachment of the GRGDY peptide onto the primary amino groups of the bulk polymer synthesized in Example 3.

The polymer from Example 3 (102 mg) was dissolved in 1 ml of dichloromethane and then 1.5 ml of dimethylsulfoxide was added. The GRGDY peptide (1.15 mg, 2.0 mol) was dissolved in 1 ml of dimethylsulfoxide. A solution of carbonyldiimidazole (CDI) was prepared in dichloromethane at a concentration of 10 mg/ml, 0.0627 mmol/ml. The polymer and peptide solutions were combined, and then, 0.375 ml (equivalent to 23.1 mol) of the 10 mg/ml solution of CDI was added over a 4 hour period. The dicholoromethane was removed by evaporation and 5 ml of water was added. The polymer precipitated and was collected by vacuum filtration. Amino acid analysis of the peptide modified sample yielded 3 mmol of peptide/g of polymer. Appropriate controls contained no peptide.

EXAMPLE 7

GRGDY-peptide attachment to processed films from Example 4.

This is an example of modifying the surface of solvent cast films from Example 4 with the GRGDY adhesion peptide.

Solvent cast films from. Example 3 were immersed in 10% aqueous acetone for one hour and then rinsed in 0.01N pyridine. Next the films were activated with glutaraldehyde (5% in 0.01N aqueous pyridine buffer, pH=6.0) for 3 hours, rinsed with 0.01N pyridine, pH 6.0 for 1–2 minutes and then exposed to the GRGDY peptide (0.5 mg/ml in PBS, pH 7.2) for 16 hours. After 16 hours, the films were rinsed for 2 minutes each in a series of 6 buffers or water: 0.01N pyridine, pH 6.0; deionized water; 0.1M sodium acetate, pH 5.5; 1M sodium chloride; phosphate buffered saline, pH 7.2; and deionized water (in that order).

EXAMPLE 8

Cell adhesion to modified films from Example 7.

This example illustrates the ability of cells to adhere the peptide modified films from Example 7.

The films from example 7 were sterilized by exposure to ultraviolet radiation for 15 minutes on each side and then placed in a sterile cell adhesion apparatus. The wells were filled with 0.4 ml of serum-free Dulbecco's Modified Eagle Medium and 3T3 mouse fibroblasts were added to the medium so that the initial density was approximately 10,000 cells/cm$^2$. The cells were incubated at 37° C. for 4 hours, then washed 3 times with Hanks Balanced Salt Solution, and the remaining cells were visually counted. The percentage of cells that remained on the peptide modified surface was higher ($26\pm1\%$, n=6) than on untreated surfaces ($6\pm8\%$, n=6).

Modifications and variations of the present invention will be obvious to those skilled in the art from the foregoing detailed description. Such modifications and variations are intended to come within the scope of the appended claims.

We claim:

1. a biodegradable, biocompatible polymer formed by polymerizing a morpholinedione, wherein the morpholinedione is a dimer of
   (i) an α-hydroxy acid of the formula R, R'—COH—CO—OH wherein R and R' are independently H or a linear or branched alkyl; and
   (ii) an α-amino acid of the formula R", R'''—CNH$_2$—CO—OH wherein R" and R'" are independently H or a linear or branched alkyl; a protected primary or secondary amino group; a protected ester; a protected hydroxyl; a protected sulfide; a protected amide; a protected guanidino; or a protected imidazole.

2. The polymer of claim 1 wherein the α-hydroxy acids are selected from the group consisting of lactic acid, glycolic acid, hydroxybutyric acid, and valeric acid.

3. The polymer of claim 1 wherein the amino acid is N-e-protected lysine.

4. The polymer of claim 1 wherein biologically active moieties are coupled to free carboxylic acids, amino groups, sulfide groups, guanidino, imidazole or hydroxyl groups on the amino acids.

5. The polymer of claim 4 wherein the biologically active moieties are selected from the group consisting of GRGDY, YIGSR and other RGD peptides.

6. A process for making a biocompatible, biodegradable polymer comprising:
   (A) forming a morpholinedione by chemically coupling
   (i) an α-amino acid of the formula R", R'''—CNH$_2$—CO—OH, wherein R" and R'" are independently H or a linear or branched alkyl; a protected primary or secondary amino group; a protected ester; a protected hydroxyl; a protected sulfide; a protected amide; a protected guanidino; or a protected imidazole; and
   (ii) an α-hydroxy acid of the formula R,R'—COH—CO—OH, wherein R and R' are independently H or a linear or branched alkyl; and
   (B) polymerizing the morpholinedione with a Lewis acid.

7. The process of claim 6 wherein the α-hydroxy acids are selected from the group consisting of lactic acid, glycolic acid, hydroxybutyric acid, and valeric acid.

8. The process of claim 1 wherein the amino acid is N-e-protected lysine.

9. The process of claim 1 further comprising coupling biologically active moieties to free carboxylic acids, amino groups, sulfide groups, guanidino, imidazole or hydroxyl groups on the amino acids.

10. The process of claim 9 wherein the biologically active moieties are selected from the group consisting of GRGDY, YIGSR and other RGD peptides.

11. The process of claim 9 further comprising forming the polymer into a matrix for seeding with cells.

12. The process of claim 11 further comprising seeding the matrix with cells.

13. A method for implanting cells into an animal comprising
   (A) forming a matrix of a biocompatible, biodegradable polymer formed by polymerizing a morpholinedione wherein the morpholinedione is a dimer of
   (i) an α-hydroxy acid of the formula R,R'—COH—CO—OH, wherein R and R' are independently H or a linear or branched alkyl; and
   (ii) an α-amino acid of the formula R",R'''—CNH$_2$—CO—OH, wherein R" and R'" are independently H or a linear or branched alkyl; a protected primary or secondary amino group; a protected ester; a protected hydroxyl; a protected sulfide; a protected amide; a protected guanidino; or a protected imidazole, and
   (B) seeding the matrix with cells.

14. The method of claim 13 further comprising deprotecting protected amino, ester, hydroxyl, sulfide, amide, guanidino or imidazole groups on the polymer, and coupling biologically active moieties to free carboxylic acid, amino groups, sulfide groups, guanidino, imidazole or hydroxyl groups on the amino acids.

15. The process of claim 13 wherein the α-hydroxy acids are selected from the group consisting of lactic acid and glycolic acid.

16. The process of claim 13 wherein the amino acid is lysine.

17. The process of claim 13 wherein the biologically active moieties are selected from the group consisting of GRGDY, YIGSR and other RGD peptides.

18. The process of claim 13 wherein the cells are selected from the group consisting of hepatocytes, pancreatic cells, intestinal cells, uroendothelial cells, skin cells, muscle cells, nerve cells, and bone cells.

19. The process of claim 13 further comprising implanting the matrix seeded with cells.

20. The biocompatible biodegradable polymer of claim 1 further comprising biologically active moieties chemically coupled to the polymer.

21. The polymer of claim 20 wherein the biologically active moieties are attachment peptides.

22. The polymer of claim 1 wherein the protecting groups on the α-amino acid are deprotected.

23. The method of claim 6 further comprising deprotecting the protecting groups on the α-amino acid.

* * * * *